(12) United States Patent
Nackaerts et al.

(10) Patent No.: US 8,872,520 B2
(45) Date of Patent: Oct. 28, 2014

(54) SENSOR AND MEASUREMENT METHOD

(75) Inventors: Axel Nackaerts, Heverlee (BE);
Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 347 days.

(21) Appl. No.: 13/010,732

(22) Filed: Jan. 20, 2011

(65) Prior Publication Data
US 2011/0175595 A1 Jul. 21, 2011

(30) Foreign Application Priority Data

Jan. 21, 2010 (EP) .................................... 10151337

(51) Int. Cl.
G01N 27/02 (2006.01)
G01N 27/416 (2006.01)
G01N 27/403 (2006.01)
G01N 27/414 (2006.01)

(52) U.S. Cl.
CPC .................................. G01N 27/414 (2013.01)
USPC ............................ 324/439; 324/438; 257/253

(58) Field of Classification Search
CPC ............... G01N 27/414; G01N 27/403; C12Q 2565/607; H01L 27/088
USPC .................. 324/111, 438, 439, 446; 257/253; 702/55
See application file for complete search history.

(56) References Cited

U.S. PATENT DOCUMENTS

| | | | | |
|---|---|---|---|---|
| 4,284,905 A * | 8/1981 | Rosenzweig | .................. | 326/88 |
| 5,684,487 A | 11/1997 | Timko | | |
| 6,724,239 B2 * | 4/2004 | Price et al. | ..................... | 327/536 |
| 7,435,610 B2 | 10/2008 | Hsiung et al. | | |
| 7,608,810 B2 * | 10/2009 | Yamada | ..................... | 250/214 R |
| 2004/0077116 A1 * | 4/2004 | Hsiung et al. | ................... | 438/48 |
| 2006/0046375 A1 | 3/2006 | Chou et al. | | |
| 2007/0155037 A1 | 7/2007 | Chou et al. | | |
| 2009/0072800 A1 * | 3/2009 | Ramadass et al. | ............. | 323/271 |
| 2009/0127589 A1 * | 5/2009 | Rothberg et al. | ............. | 257/253 |
| 2011/0036913 A1 | 2/2011 | Merz et al. | | |
| 2011/0208457 A1 | 8/2011 | Merz et al. | | |

FOREIGN PATENT DOCUMENTS

GB 2 406 175 A 3/2005

OTHER PUBLICATIONS

Extended European Search Report for European Patent Appln. No. 10151337.2 (Jul. 13, 2010).

* cited by examiner

*Primary Examiner* — Patrick Assouad
*Assistant Examiner* — Hoang X Nguyen

(57) ABSTRACT

The present invention relates to a sensor comprising a substrate (10) carrying a field effect transistor (30) having a gate electrode (32), the sensor further comprising a measurement electrode (36) spatially separated from the gate electrode; and a reference electrode (40), said measurement electrode being in configurable conductive contact with said gate electrode, the sensor further comprising a charge storage element (60) comprising a first electrode connected to a node (38) between the measurement electrode and the gate electrode; and a second electrode configurably connected to a known potential source (80). The present invention further relates to a method of performing a measurement with such a sensor.

20 Claims, 5 Drawing Sheets

SENSOR AND MEASUREMENT METHOD

CROSS-REFERENCE TO RELATED APPLICATIONS

This application claims the priority under 35 U.S.C. §119 of European patent application no. 10151337.2, filed on Jan. 21, 2010, the contents of which are incorporated by reference herein.

FIELD OF THE INVENTION

The present invention relates to a sensor comprising a substrate carrying a field effect transistor comprising a gate electrode, the sensor further comprising a measurement electrode spatially separated from the gate electrode and a reference electrode, said measurement electrode being in conductive contact with said gate electrode.

The present invention further relates to a method of performing a measurement with such a sensor.

BACKGROUND OF THE INVENTION

It is known that field effect transistors (FETs) may be used as sensors, e.g. by functionalizing the gate electrode electrode of the FET, e.g. by coating with or forming it from a substance that can interact with an analyte of interest, such that the operation of the FET becomes sensitive to chemical compounds or particles of interest. For instance, the current flowing through the FET in such applications may be typically dependent on the concentration of the chemical compound of interest in a medium brought into contact with the gate electrode electrode of the FET.

Several different types of FETs have been developed for this purpose, such as a ChemFET, which is typically sensitive to chemical compounds, and an ISFET, which is sensitive to specific types of ions. One of the benefits of having FET-based sensors is that the sensor may be integrated in an integrated circuit (IC), such that the sensor signal processing components can be provided on the same die, thus yielding a compact arrangement.

Another example of a FET-based sensor is the extended gate electrode FET (EGFET), which is shown in FIG. 1. The FET 30 is formed in a substrate 10, and has a gate electrode 32 that is connected to a measurement electrode 36 via a conductive connection 34 through for instance a protective layer 20 such as a dielectric layer for protecting the circuitry on the substrate 10 from exposure to the medium 50. A reference electrode 40 is also present. Both the measurement electrode 36 and the reference electrode 40 are in contact with a medium 50 containing the analyte of interest in a concentration to be determined from the current through the FET 30 as controlled by the gate electrode voltage, which, due to the connection 34 between the gate electrode 32 and the measurement electrode 36 is a reproduction of the potential induced by the analyte of interest being sensed by the measurement electrode, e.g. through chemical binding with the measurement electrode plus the potential (bias) on the reference electrode 40. The FET 30 will start exhibiting a current flowing though the device when the gate electrode voltage exceeds the threshold voltage $V_T$ of the FET 30. The FET 30 is referred to as an EGFET because of the fact that the measurement electrode 36 acts as a gate electrode extension of the FET 30.

One of the problems with a sensor as shown in FIG. 1 is that the potential difference between the measurement electrode 36 and the reference electrode caused by the medium 50 may not be large enough to exceed $V_T$. In such a scenario, the sensor may have insufficient sensitivity. A straightforward solution to this problem is to bias the gate electrode 32 and the measurement electrode 36 by applying a (DC) voltage to the reference electrode 40, thereby effectively lowering $V_T$. This, however, has the drawback that a current may run through the medium 50 if the measurement and reference electrodes in the analyte and surrounding surfaces are not insulated properly, which may cause unwanted electrochemical reactions resulting in sensor drift or corrosion.

SUMMARY OF THE INVENTION

The present invention seeks to provide a sensor according to the opening paragraph having sufficient sensitivity without causing a current to run though the medium.

The present invention further seeks to provide a method of performing a measurement with such an improved sensor.

According to a first aspect of the present invention, there is provided a sensor comprising a substrate carrying a field effect transistor having a gate electrode, the sensor further comprising a measurement electrode spatially separated from the gate electrode and a reference electrode, said measurement electrode being in conductive contact with said gate electrode, the sensor further comprising a charge storage element comprising a first electrode configurably connected to a node between the measurement electrode and the gate electrode and a second electrode configurably connected to a known potential source.

The present invention has been based on the realization that the measurement value, i.e. the potential difference between the measurement electrode and the reference electrode may be stored as an amount of charge in a charge storage element such as a capacitor, which may be disconnected from the measurement electrode when driving the gate electrode of the FET with a voltage induced by the charge stored in the charge storage element. Hence, this allows for biasing, i.e. driving, the charge storage element during the read-out cycle without this affecting the medium due the fact that the measurement electrode is conductively disconnected from the gate electrode and charge storage element during this read-out cycle. Consequently, a more sensitive sensor is achieved simply by choosing a charge storage element with a large enough capacity to drive the gate electrode of the FET.

In a preferred embodiment, the sensor comprises a first switch between the measurement electrode and said node, a second switch between the second electrode and the known potential source, and a third switch between the second electrode and a further known potential source.

The known potential source is typically a potential having a lower value than the measurement potential, i.e. the potential across the measurement electrode and the reference electrode, whereas the further known potential is typically a potential having a higher value than the measurement potential, such that during the data acquisition cycle, the charge storage element may be connected between the measurement electrode and the known potential source, thus charging the charge storage element with a charge representative of the measurement potential. In the read-out phase, the charge storage element is connected between the gate electrode and the further known potential source such that the resulting potential sensed by the gate of the FET exceeds the threshold voltage of the FET, thereby ensuring that the FET is always switched on when a measurement potential has been stored on the charge storage element. Preferably, the fixed potential source is ground and the further fixed potential source is a supply voltage source.

In an embodiment, at least one of the first, second and third switch is implemented by a pass gate.

In an other embodiment, the first and second switch are controlled by a first control signal, and the third switch is controlled by a further control signal, the first and further control signals being non-overlapping. In this context, non-overlapping means that the first and second switches on the one hand and the third switch on the other hand are not simultaneously enabled. This has the advantage that a very simple implementation for switching between the data acquisition cycle and the read-out cycle is achieved.

In yet another embodiment, the first, second and third switch are controlled by independent control signals, which has the advantage of a further reduction of the transient current that may occur between the measurement electrode and the reference electrode. The respective control signals preferably are clock signals.

In the sensor of the present invention, the field effect transistor may be an extended gate electrode field effect transistor, although any FET having a measurement electrode separated from and in conductive contact with the gate electrode of the FET may be used. The sensor may be a pH sensor.

The sensor of the present invention may form part of an IC, which may further comprise signal processing circuitry for processing the sensor signal. The sensor or IC of the present invention may be included into an apparatus, which may be any apparatus for sensing or measuring the presence or concentration of an analyte of interest. For instance, the apparatus may be a diagnostic apparatus to be used in the field of medicine for measuring the presence or concentration of an analyte of interest in a bodily fluid of a patient. Alternatively, the apparatus may be a sensing device for use in environmental control, for measuring the concentration of an analyte of interest in e.g. waste streams or closed environments such as dwellings. The apparatus may be designed for industrial purposes for measuring the presence or concentration of an analyte of interest in an industrial process. Many other application domains will be apparent to the skilled person.

The apparatus may comprise a sample chamber, with the measurement electrode and the reference electrode being at least partially located inside the sample chamber.

In accordance with a further aspect of the present invention, there is provided a method of performing a measurement with the sensor of the present invention, the method comprising connecting the charge storage element to the measurement electrode in a data acquisition stage of said measurement, for storing a measurement voltage in said charge storage element; disconnecting the charge storage element from the measurement electrode; and reading out the measurement voltage from the charge storage element with the field effect transistor.

By using the measurement electrode to charge the charge storage element in accordance with the measurement voltage rather than driving the gate electrode, and disconnecting the measurement electrode from the gate electrode and the charge storage element prior to the read-out of the charge storage element, the medium 50 is not subjected to a current resulting from the potential difference between the charge storage element and the reference electrode, such that an improved sensor in terms of sensitivity is obtained.

In an embodiment, the sensor comprises a first switch between the measurement electrode and said node, a second switch between the second electrode and the known potential source, and a third switch between the second electrode and a further known potential source, and wherein during said data acquisition stage the first switch and the second switch are conducting and the third switch is non-conducting; and during said reading out stage, the first switch and the second switch are non-conducting and the third switch is conducting.

This may be achieved by applying a first clock signal to the first switch and the second switch for switching the first switch and a second switch between said conducting and non-conducting states; and applying a further clock signal to the third switch for switching the third switch between said conducting and non-conducting states, wherein a conducting state induced by the first clock signal does not overlap with a conducting state induced by the further clock signal.

In other words, the clock signal and the further clock signal may be non-overlapping, which ensures that the implementation of the control signals for controlling the respective switches is relatively simple.

The method may further comprise amplifying the read out signal produced by the field effect transistor during the read-out cycle.

BRIEF DESCRIPTION OF THE EMBODIMENTS

Embodiments of the invention are described in more detail and by way of non-limiting examples with reference to the accompanying drawings, wherein FIG. 1 schematically depicts a prior art sensor;

FIG. 2 schematically depicts a sensor in accordance with an embodiment of the present invention;

FIG. 3 schematically depicts a sensor in accordance with another embodiment of the present invention;

DETAILED DESCRIPTION OF THE DRAWINGS

Figure 1:
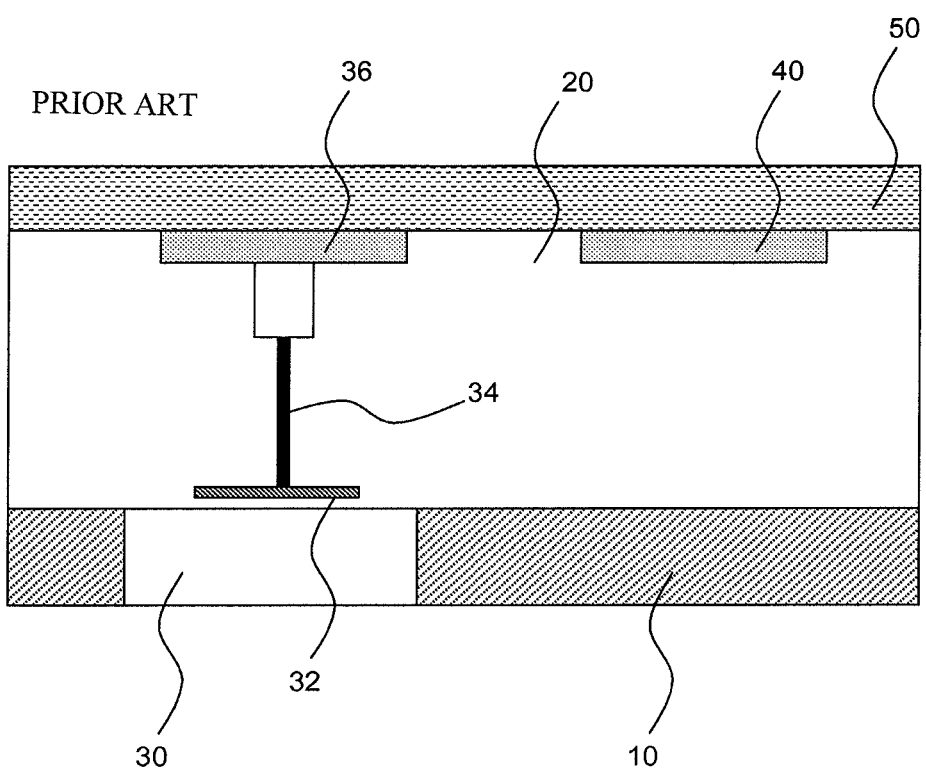

It should be understood that the Figures are merely schematic and are not drawn to scale. It should also be understood that the same reference numerals are used throughout the Figures to indicate the same or similar parts.

Figure 2:
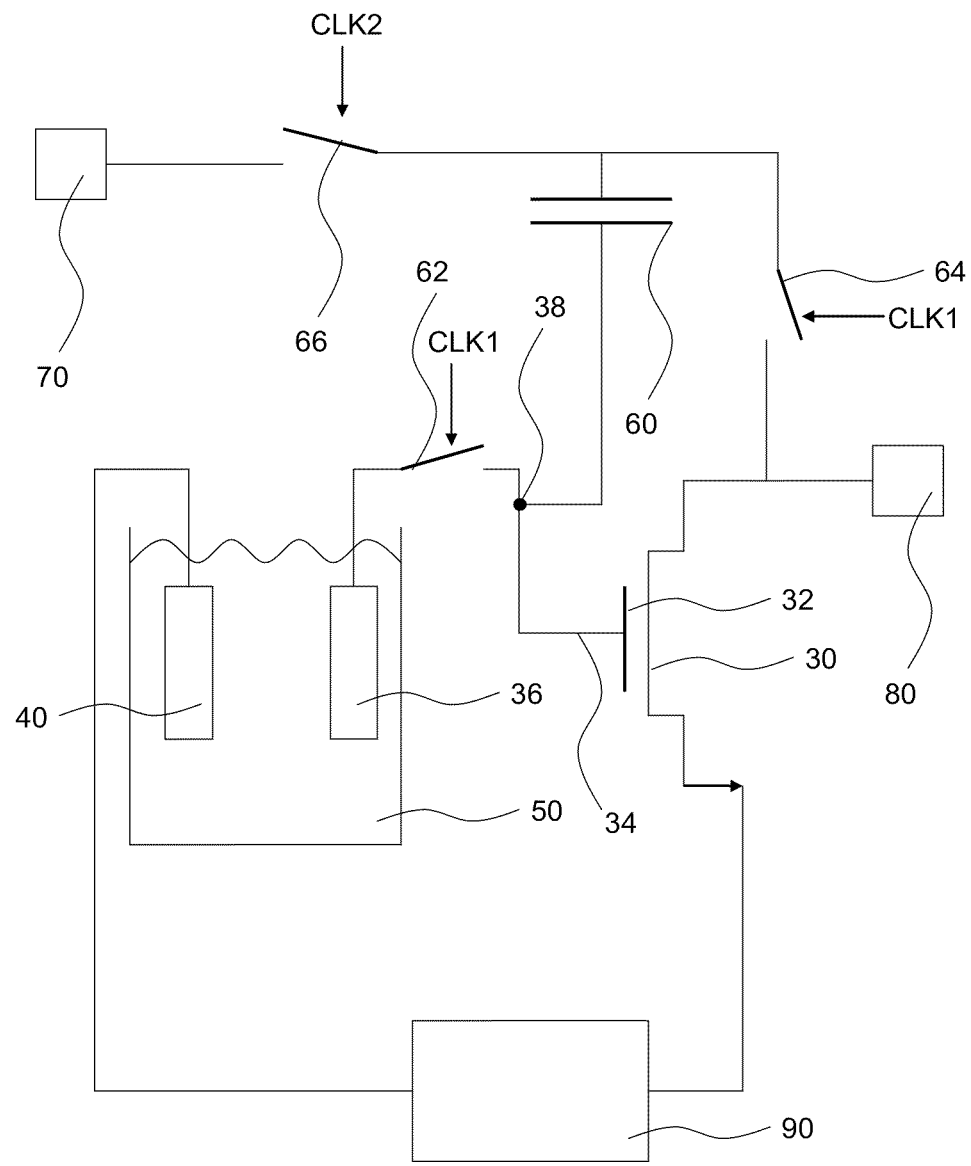

FIG. 2 shows a first embodiment of a sensor in accordance with the present invention. In this embodiment, the measurement electrode 36 is configurably coupled to the gate electrode 32 of the FET 30 via a conductive path 34 comprising a first switch 62 under control of a first control signal CLK1. A charge storage element 60 is further conductively coupled to node 38 between the first switch 62 and the gate electrode 32.

The charge storage element 60 is further conductively coupled to a second switch 64 under control of the first control signal CLK1, which configurably connects the charge storage element 60 to a first potential source 80, and a second switch 64 under control of the second control signal CLK2, which configurably connects the charge storage element 60 to a second potential source 70.

In a preferred embodiment, the charge storage element 60 is implemented as a capacitor stage, which may comprise one or more capacitors. The total capacitance of the capacitor stage is chosen based on the threshold voltage $V_T$ of the FET 30. More precisely, the capacitance is chosen such that it is large enough to generate a voltage exceeding $V_T$ when charged by a potential difference between the measurement electrode 36 and the reference electrode 40 caused by a concentration of the analyte of interest in the medium 50 that should be detectable by the sensor. This potential difference will also be referred to as the measurement voltage $V_M$.

In case of the charge storage element 60 comprising a capacitor stage, the first switch 62 and the gate electrode 32 are conductively coupled to a first plate or electrode of the capacitor, whereas the second switch 64 and the third switch 66 are conductively coupled to a second electrode or plate of the capacitor stage. The capacitor stage may be implemented in any suitable manner in the sensor of the present invention. For instance, the capacitor stage may be formed in the substrate 10 shown in FIG. 1. Alternatively, in case of the sensor forming part of an IC, the capacitor stage may be formed in the metallization layers that form the conductive connections to the various devices in the IC including the FET 30, with the respective plates of the capacitor stage being formed in different metallization layers, with the dielectric layer separating the metallization layers forming the dielectric of the capacitor stage. It should be understood that these are non-limiting examples only, and that many implementations of capacitor stages in integrated circuits are readily available to the skilled person.

In operation, the sensor shown in FIG. 2 has two distinct operation periods, which will be referred to as stages in the remainder of this description. The first stage is a data acquisition stage, in which the first switch 62 and the second switch 64 are closed, i.e. switched to a conductive state, and the third switch 66 is open, i.e. switched to a non-conductive state. This connects the data storage element 60 between the measurement electrode 36 and the first potential source 80.

The first potential source 80 is a known potential source having a potential that is lower than the measurement potential $V_M$ of the measurement electrode 36, such that the resulting voltage across the charge storage element 60 charges the charge storage element 60 until charge on the electrode of the charge storage element 60 that is conductively coupled to the measurement electrode 36 via the first switch 62 reflects the measurement potential $V_M$. In the context of the present invention, a known potential source is a potential source that delivers a well-defined and preferably constant potential at least during operation of the sensor.

The second stage in the operation of the sensor of the present invention may be called a read-out stage, in which the charge stored in the charge storage element 60 is used to drive the FET 30, such that the resulting current through the FET 30 is representative of $V_M$, i.e. the concentration of the analyte of interest in the medium 50. To this end, the first switch 62 and the second switch 64 are opened, and the third switch 66 is closed, thereby connecting the charge storage element 60 to the second potential source 70, which should produce a constant potential $V_P$ having a value of at least $V_T$, such that the gate voltage $V_G$ sensed by the gate electrode 32 equates to $V_G = V_P + V_M$. Because $V_M \geq 0V$, this ensures that $V_G$ exceeds $V_T$ such that the FET 30 is always switched on when $V_M > 0V$, i.e. when a non-zero concentration of the analyte of interest has been measured in the medium 50.

The known potential source 80 may be ground (GND), and the second known potential source 70 may be the supply voltage $V_{DD}$. However, it should be understood that other values of the first known potential source 80 and the second known potential source 70 may be chosen without departing from the present invention. For instance, in case the FET 30 reaches saturation for $V_G \sim V_{DD}$, a smaller voltage may be provided as the further fixed potential, which may be a fraction of the supply voltage, e.g. $0.5*V_{DD}$, as long as this fraction has a magnitude of at least $V_T$.

Upon completion of the read-out stage, the operation of the sensor may proceed to in the next data acquisition stage, in which the third switch 66 is opened again and the first switch 62 and the second switch 64 are closed again. At this point, it is noted that the (dis)charging of the data storage element 60 requires a transient current to run from the reference electrode 40 and the measurement electrode 36, with the magnitude of this current being determined by the size, e.g. capacitance, of the charge storage element 60. However, it is pointed out that the amount of this current is substantially smaller than the DC current that is the result of biasing the measurement electrode 36 in the prior art sensor shown in FIG. 1.

In an embodiment of the present invention, the first switch 62 and the second switch 64 are closed at the same time, whilst the third switch 66 must not be closed whilst the first switch 62 and second switch 64 are closed, and vice versa. Hence, the first switch 62 and the second switch 64 may be controlled by a first control signal, with the third switch 66 being controlled by a further control signal that preferably is the logical complement of the first control signal, at least when the switches 62, 64 and 66 are of the same conductivity type. More generally speaking, the first control signal and the second control signal are non-overlapping in this embodiment, which means that the control signals are shaped such that at no point in time the first switch 62 and the second switch 64 are conductive when the third switch 66 is conductive, and vice versa.

In FIG. 2, the switches 62, 64, 66 are controlled by respective clock signals labeled CLK1 and CLK2 respectively. It should however be understood that the first control signal and the second control signal may be any suitable non-overlapping control signal.

In FIG. 2, further circuitry 90 is depicted, which for instance may comprise an amplifier for amplifying the current generated by the FET 30 during the read-out stage. The further circuitry 90 may further comprise a fixed potential source for providing the reference electrode with a reference voltage. Other circuitry, such as signal processing circuitry for converting the (amplified) current through the FET 30 into an analyte concentration value, may also be present.

The sensor of the present invention may be integrated in an apparatus comprising a sample chamber, in which at least part of the measurement electrode 36 and the reference electrode 40 of the sensor are exposed to the medium 50, e.g. a fluid sample potentially comprising the analyte of interest. In order for the measurement electrode 36 to be sensitive to the analyte of interest, i.e. exhibit a change in potential upon interaction with the analyte, the measurement electrode 36 may be made of a material or a combination of materials with known sensitivity to the analyte of interest. Alternatively, the measurement electrode may be functionalized, e.g. coated, with a compound known to be able to interact with the analyte of interest, thereby changing the measurement potential of the measurement electrode 36.

Although not explicitly shown in FIG. 2, the sensor of the present invention may be manufactured as an integrated circuit, in which the measurement electrode 36 is separated from the gate electrode 32 by at least one insulating layer, which may be made of any suitable dielectric material, such as $SiO_2$, $Si_3N_4$ or any suitable low-k dielectric. The at least one insulating layer may be a part of a stack of layers, such as a metallization stack comprising patterned metal layers separated by dielectric layers. Other layer stacks are also feasible. The conductive path 34 may be realized in any suitable manner, e.g. including one or more vias.

In an embodiment, the sensor of the present invention comprises at least one insulating layer between the measurement electrode 36 and the FET 30 including the gate electrode 32, wherein the measurement electrode 36 and the reference electrode 40 are exposed on a surface of the at least one insulating layer.

Figure 3:
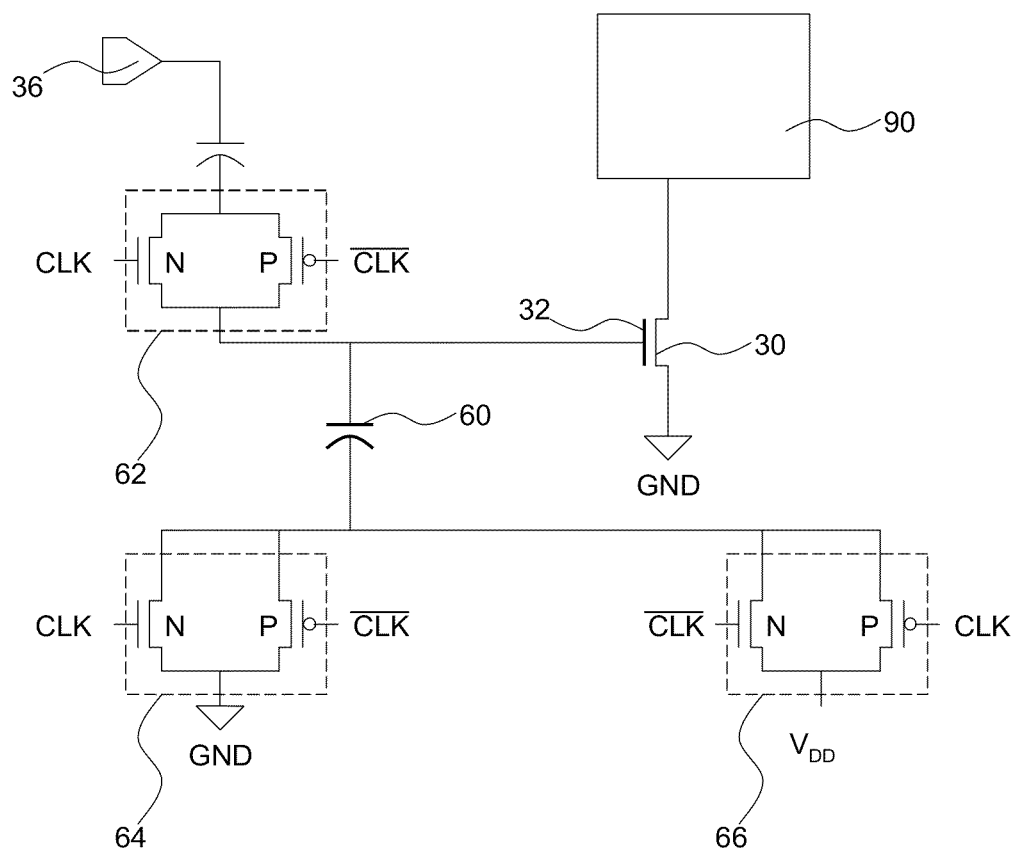

The switches 62, 64, 66 may be implemented in any suitable manner. For instance, as shown in FIG. 3, the first switch 62, the second switch 64 and the third switch 66 are all implemented as pass gates, which comprise a pMOS transistor labeled P and an nMOS transistor labeled N. The use of pass gates has the advantage that the charge storage element 60 can be readily charged as well as discharged, such that the potential of the sample 50 can be readily followed, thus avoiding unwanted source/drain to substrate leakage when the potential of the sample 50 is lower than a bias applied to the substrate 10. It is noted that this problem becomes negligible at sampling rates in the kHz domain, and does not exist in insulated substrate technologies, e.g. silicon-on-insulator substrates. In this embodiment, the nMOS transistors are controlled by a clock signal CLK and the pMOS transistors are controlled by the inverted clock signal $\overline{CLK}$. In FIG. 3, the first potential source 80 is depicted as ground (GND) and the second potential source 70 is depicted as a supply voltage source $V_{DD}$ by way of non-limiting example only.

Figure 4:
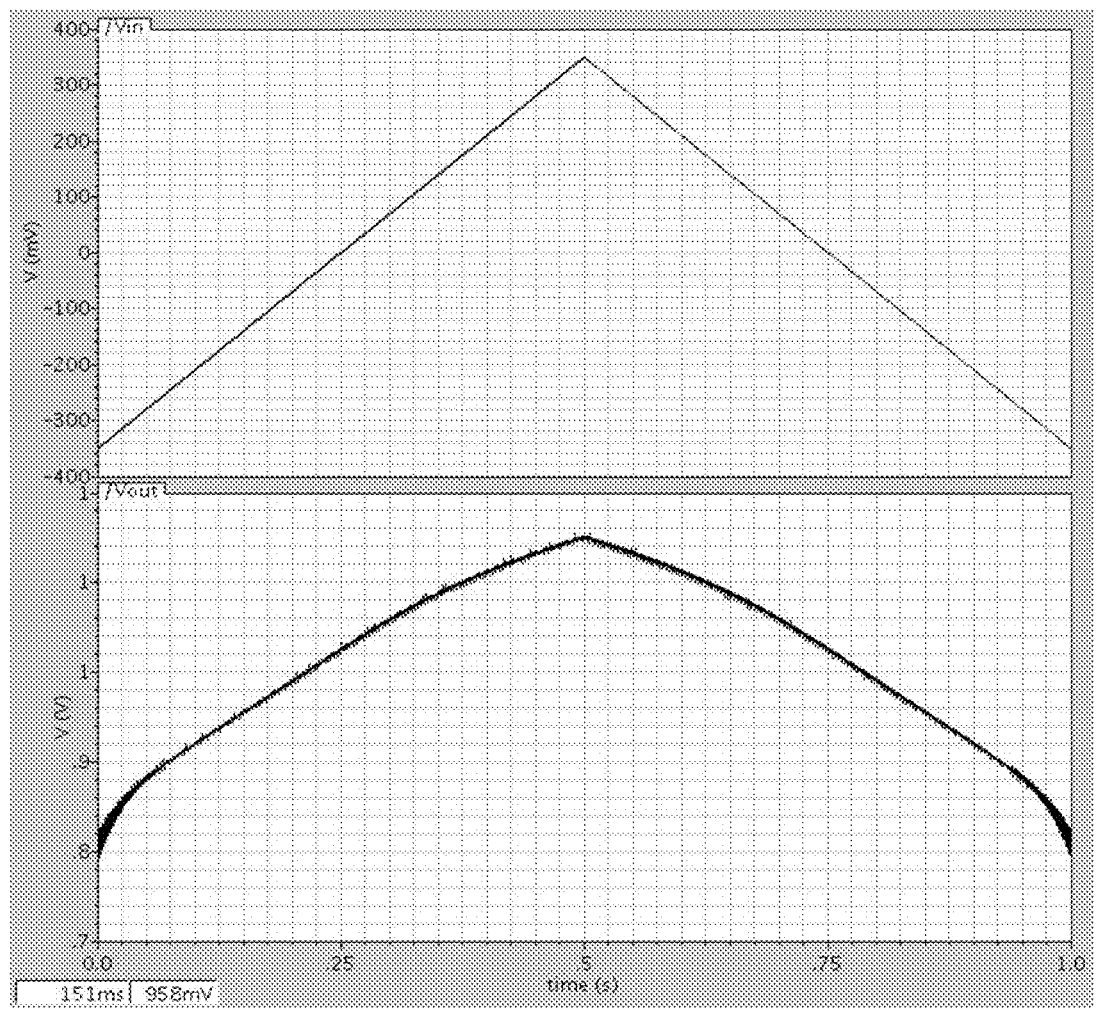
FIG. 4 depicts a simulated output signal of a sensor in accordance with an embodiment of the present invention.

FIG. 4 depicts the output of the FET 30 of the sensor of FIG. 2 (bottom curve) as a function of the time-varying potential of the measurement electrode 36 (top curve). In FIG. 4, the output of the FET 30 has been amplified, and the sample rate of the sensor is 100 kHz. For the sake of clarity, it is pointed out that one sample period comprises a single data acquisition stage followed by a single read-out stage. As is clearly shown in FIG. 4, the FET 30 becomes responsive to the potential on the measurement electrode for negative values of $V_M$, i.e values well below the $V_T$ of the FET 30, thereby demonstrating that the sensor of the present invention has an improved sensitivity compared to the prior art sensor shown in FIG. 1.

Figure 5:
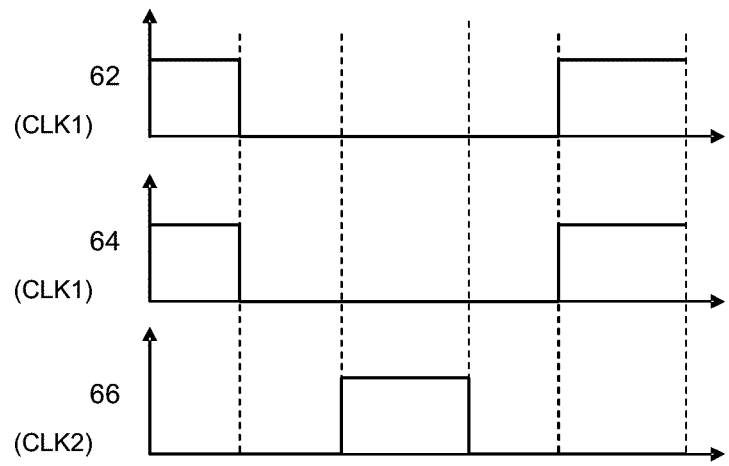
FIG. 5 depicts a timing diagram of control signals for controlling a sensor in accordance with an embodiment of the present invention.

FIG. 5 shows a timing diagram of the control signals of the first switch 62, the second switch 64 and the third switch 66, in which the first switch 62 and the second switch 64 share the control signal CLK1, with the third switch 66 being controlled by a further control signal CLK 2. As previously mentioned, these control signals may be clock signals, although this is not essential. The switches are in a conductive state when the respective control signals CLK 1, CLK 2 are high. FIG. 5 clearly depicts that control signal CLK 2 has no overlap with control signal CLK 1, i.e. is not in a high state at the same time, such that the charging of the charge storage element 60 is separated in time from the driving of the gate electrode 32 of the FET 30.

Figure 6:
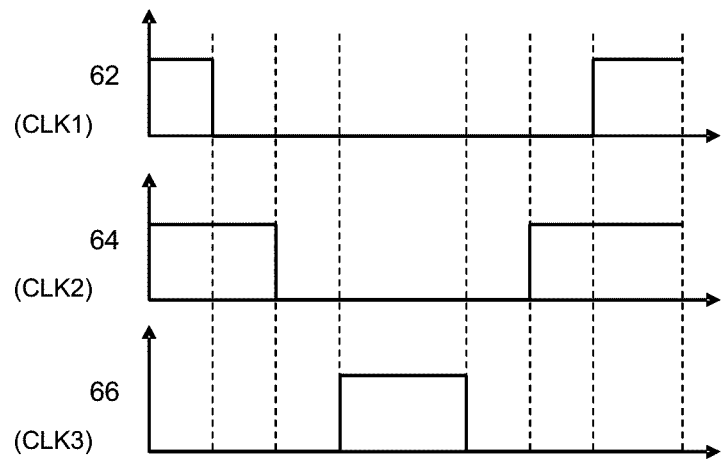
FIG. 6 depicts a timing diagram of control signals for controlling a sensor in accordance with another embodiment of the present invention.

It is however not necessary that the first switch 62 and the second switch 64 share a control signal. An alternative embodiment is shown in FIG. 6, in which the first switch 62 is controlled by a first control signal CLK1, the second switch 64 is controlled by a second control signal CLK2 and the third switch 66 is controlled by a third control signal CLK3. The switches are in a conductive state when the respective control signals CLK 1, CLK 2 and CLK3 are high The first and second control signals CLK1 and CLK2 should have an overlap, i.e. a time period in which both the first switch 62 and the second switch 64 are conducting, which time period should not overlap with the time period in which the third switch 66 is conducting, as previously explained.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A sensor comprising a substrate carrying a field effect transistor having a gate electrode, the sensor further comprising:
a measurement electrode spatially separated from the gate electrode, the measurement electrode being in configurable conductive contact with the gate electrode;
a reference electrode;
a charge storage element including a first electrode connected to the gate electrode via a node between the measurement electrode and the gate electrode and a second electrode configurably connected to a known potential source, the charge storage element being configured and arranged to drive the gate electrode with a voltage induced by a charge on the charge storage element during a read-out cycle of the sensor; and
switching circuitry configured and arranged to connect the charge storage element to the measurement electrode during a data acquisition cycle of the sensor, and in response the measurement electrode reaching a measurement potential, connect the charge storage element to a second potential source during the read-out cycle of the sensor.

2. The sensor of claim 1, wherein the gate electrode is connected to the first electrode via a node between the measurement electrode and the gate electrode, wherein the switching circuitry includes a first switch between the measurement electrode and said node, a second switch between the second electrode and the known potential source, and a third switch between the second electrode and a further known potential source, and wherein the charge storage element is further configured and arranged to drive the gate electrode of the field effect transistor with a current resulting from the measurement potential that is indicative of a concentration of an analyte of interest during the read-out cycle of the sensor, and the charge storage element is connected between the measurement electrode and the known potential during the data acquisition cycle of the sensor.

3. The sensor of claim 2, wherein at least one of the first, second and third switch is implemented as a pass gate, and the charge storage element is charged until a charge on the first electrode is equal to the measurement potential.

4. The sensor of claim 2, wherein, in operation, the first and second switch are controlled by a first control signal, and the third switch is controlled by a further control signal, the first and further control signals being non-overlapping.

5. The sensor of claim 2, wherein the first, second and third switches are controlled by separate control signals.

6. The sensor of claim 5, wherein the respective control signals are clock signals.

7. The sensor of claim 2, wherein the known potential source is ground and the further known potential source is a supply voltage source.

8. The sensor of claim 1, wherein the field effect transistor is an extended gate electrode field effect transistor.

9. An apparatus comprising a sensor as claimed in claim 1.

10. The apparatus of claim 9, wherein the apparatus comprises a sample chamber, with the measurement electrode and the reference electrode being at least partially located inside the sample chamber.

11. The sensor of claim 1, wherein the charge storage element is further configured and arranged to generate the voltage in response to a potential difference between the measurement electrode and the reference electrode.

12. The sensor of claim 11, wherein the potential difference is caused by a concentration of an analyte of interest, that is detectable by the sensor, in a medium.

13. The sensor of claim 1, wherein the read-out cycle of the sensor is prompted in response to a non-zero concentration of an analyte of interest, that is detectable by the sensor, in a medium.

14. A method of performing a measurement with a sensor including a substrate carrying a field effect transistor having a gate electrode, the method comprising:
   providing a measurement electrode spatially separated from the gate electrode and a reference electrode, the measurement electrode being in configurable conductive contact with the gate electrode;
   providing a charge storage element, including a first electrode connected to the gate electrode via a node between the measurement electrode and the gate electrode and a second electrode configurably connected to a known potential source, the charge storage element being configured and arranged to drive the gate electrode with a voltage induced by a charge on the charge storage element during a read-out cycle of the sensor;
   connecting the charge storage element to the measurement electrode via switching circuitry in a data acquisition stage of said measurement for storing a measurement voltage in said charge storage element;
   disconnecting the charge storage element from the measurement electrode electrode via the switching circuitry; and
   connecting the charge storage element to a second potential source via the switching circuitry and reading out the measurement voltage from the charge storage element with the field effect transistor in response the measurement electrode reaching a measurement potential.

15. The method of claim 14, wherein the charge storage element is further configured and arranged to drive the gate electrode of the field effect transistor with a current resulting from a measurement potential that is indicative of a concentration of an analyte of interest during the read-out cycle of the sensor, and the charge storage element is connected between the measurement electrode and the known potential during a data acquisition cycle of the sensor, and wherein the switching circuitry includes a first switch between the measurement electrode and said node, a second switch between the second electrode and the known potential source, and a third switch between the second electrode and a further known potential source, and wherein:
   during said data acquisition stage the first switch and the second switch are conducting and the third switch is non-conducting; and
   during said reading out stage, the first switch and the second switch are non-conducting and the third switch is conducting.

16. The method of claim 15, wherein the known potential source is ground and the further known potential source is a supply voltage source, and the charge storage element is charged until a charge on the first electrode is equal to the measurement potential.

17. The method of claim 15, further comprising:
   applying a first clock signal to the first switch and the second switch for switching the first switch and a second switch between said conducting and non-conducting states; and
   applying a further clock signal to the third switch for switching the third switch between said conducting and non-conducting states,
   wherein a conducting state induced by the first clock signal does not temporally overlap with a conducting state induced by the further clock signal.

18. The method of claim 14, further comprising amplifying the read out signal produced by the field effect transistor.

19. The method of claim 14, further including generating the voltage in response to a potential difference between the measurement electrode and the reference electrode.

20. The method of claim 14, wherein generating the voltage includes causing a potential difference in response to a concentration of an analyte of interest, that is detectable by the sensor, in a medium.

* * * * *